(12) United States Patent
Sekiguchi et al.

(10) Patent No.: US 11,937,598 B2
(45) Date of Patent: *Mar. 26, 2024

(54) CERIUM OXIDE NANOPARTICLE, DECOMPOSITION METHOD OF NUCLEIC ACID, DECOMPOSITION METHOD OF POLYPEPTIDE, METHOD OF PRODUCING CERIUM OXIDE NANOPARTICLE, OXIDIZING AGENT, ANTIOXIDANT, ANTIFUNGAL AGENT, AND ANTI-VIRUS AGENT

(71) Applicant: Toray Industries, Inc., Tokyo (JP)

(72) Inventors: Shota Sekiguchi, Kamakura (JP); Kazuhiro Matsuda, Otsu (JP); Takahiro Motoshiromizu, Kamakura (JP); Masateru Ito, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 104 days.

This patent is subject to a terminal disclaimer.

(21) Appl. No.: 17/413,714

(22) PCT Filed: Dec. 17, 2019

(86) PCT No.: PCT/JP2019/049348
§ 371 (c)(1),
(2) Date: Jun. 14, 2021

(87) PCT Pub. No.: WO2020/129963
PCT Pub. Date: Jun. 25, 2020

(65) Prior Publication Data
US 2022/0030857 A1 Feb. 3, 2022

(30) Foreign Application Priority Data
Dec. 18, 2018 (JP) ................. 2018-236451

(51) Int. Cl.
| | | |
|---|---|---|
| *A01N 25/26* | (2006.01) | |
| *A01N 59/16* | (2006.01) | |
| *A01P 1/00* | (2006.01) | |
| *A01P 3/00* | (2006.01) | |
| *C01F 17/10* | (2020.01) | |
| *C01F 17/235* | (2020.01) | |
| *C09K 15/02* | (2006.01) | |
| *C09K 15/30* | (2006.01) | |

(52) U.S. Cl.
CPC ............ *A01N 25/26* (2013.01); *A01N 59/16* (2013.01); *A01P 1/00* (2021.08); *A01P 3/00* (2021.08); *C01F 17/10* (2020.01); *C01F 17/235* (2020.01); *C09K 15/02* (2013.01); *C09K 15/30* (2013.01)

(58) Field of Classification Search
CPC ...... C08L 33/24; A01N 59/16; C01P 2004/06; C01F 7/235
See application file for complete search history.

(56) References Cited

U.S. PATENT DOCUMENTS

| | | |
|---|---|---|
| 6,638,899 B1 | 10/2003 | Wakiya et al. |
| 2005/0196676 A1 | 9/2005 | Singh et al. |
| 2013/0195927 A1* | 8/2013 | Sudipta ................ A61K 33/244 |
| | | 424/617 |
| 2013/0196167 A1 | 8/2013 | Kataoka |
| 2014/0088116 A1 | 3/2014 | Morales Rojas et al. |
| 2014/0271899 A1 | 9/2014 | Leiter et al. |
| 2015/0251926 A1 | 9/2015 | Psaras et al. |
| 2016/0024351 A1 | 1/2016 | Yoshida et al. |
| 2018/0325832 A1 | 11/2018 | Bell |
| 2019/0085317 A1 | 3/2019 | Sekiguchi et al. |
| 2020/0345650 A1 | 11/2020 | Bell |

FOREIGN PATENT DOCUMENTS

| | | |
|---|---|---|
| CN | 103154167 | 6/2013 |
| CN | 106573796 | 4/2017 |
| CN | 108779455 | 11/2018 |
| JP | H11-166121 A | 6/1999 |
| JP | 2001-083713 A | 3/2001 |
| JP | 2003-213589 A | 7/2003 |
| JP | 2008-532246 A | 8/2008 |
| JP | 2016-029123 A | 3/2016 |
| JP | 2016-514163 A | 5/2016 |
| JP | 2017-514670 A | 6/2017 |
| JP | 2018-508568 A | 3/2018 |
| UA | 106101 | 7/2014 |
| WO | 2012/053497 A1 | 4/2012 |
| WO | 2015/019849 A1 | 2/2015 |
| WO | 2017/159763 A1 | 9/2017 |
| WO | 2017/174437 | 10/2017 |

OTHER PUBLICATIONS

Lakhotia et al. Nature: Scientific Reports, 2018, 8:4976, 1-10.*
Garcia et al. Prog Poly Sci, 35, 2010, 626-656.*
Shahin et al., Chem. Mater., 17, 2005, 315-321.*
Extended European Search Report dated Jul. 28, 2022, of counterpart European Application No. 19898677.0.
Chinese Office Action dated Sep. 1, 2022, corresponding to Chinese Application No. 2019800833771.2, along with an English translation.
Dodds, C. et al., Oxford Textbook of Anaesthesia for the Elderly Patient, Oct. 30, 2018, along with an English translation.

(Continued)

*Primary Examiner* — Kyle A Purdy

(74) *Attorney, Agent, or Firm* — DLA Piper LLP (US)

(57) ABSTRACT

A cerium oxide nanoparticle whose surface is covered with a vinyl polymer has a heterocyclic amine skeleton such as piperazine, pyridine, imidazole, or carbazole or with a polyamide having a heterocyclic amine skeleton such as piperazine, pyridine, imidazole, or carbazole; and a decomposition method of a nucleic acid or a polypeptide by using the cerium oxide nanoparticle.

12 Claims, 4 Drawing Sheets

(56) References Cited

OTHER PUBLICATIONS

Notice of Reasons for Refusal dated Oct. 10, 2023, of counterpart Japanese Patent Application No. 2019-570583, along with an English translation.

Fu Zhou et al., "CeO2 Sperical Crystallites: Synthesis, Formation Mechanism, Size Control, and Electrochemical Property Study," Journal of Physical Chemistry, 2007, vol. 111, pp. 1651-1657.

Atul Asati et al., "Oxidase-Like Activity of Polymer-Coated Cerium Oxide Nanoparticles," Agnew. Chem. Int. Ed., 2009, vol. 48, pp. 2308-2312.

Melissa Hirsch Kuchma, PhD et al., "Phosphate ester hydrolysis of biologically relevant molecules by cerium oxide nanoparticles," Nanomedicine: Nanotechnology, Biology, and Medicine, 2010, vol. 6, pp. 738-744.

Ying Xue et al., "Direct Evidence for Hydroxyl Radical Scavenging Activity of Cerium Oxide Nanoparticles," The Journal of Physical Chemistry, 2011, vol. 115, pp. 4433-4438.

Ruth C. Merrifield et al., "Synthesis and Characterization of Polyvinylpyrrolidone Coated Cerium Oxide Nanoparticles," Environmental Science & Technology, 2013, vol. 47, pp. 12426-12433.

Qi Wang et al., "Inhibited growth of *Pseudomonas aeruginosa* by dextran- and polyacrylic acid-coated ceria nanoparticles," International Journal of Nanomedicine, 2013, vol. 8, pp. 3395-3399.

Wensi Song et al., "Ceria Nanoparticles Stabilized by Organic Surface Coatings Activate the Lyosome-Autophagy System and Enhance Autophagic Clearance," ACS NANO, 2014, vol. 8, No. 10, pp. 10328-10342.

\* cited by examiner

R: PIPERAZINE, PYRIDINE, IMIDAZOLE, OR CARBAZOLE
R1, R2, R3: ARBITRARY SUBSTITUENT GROUPS

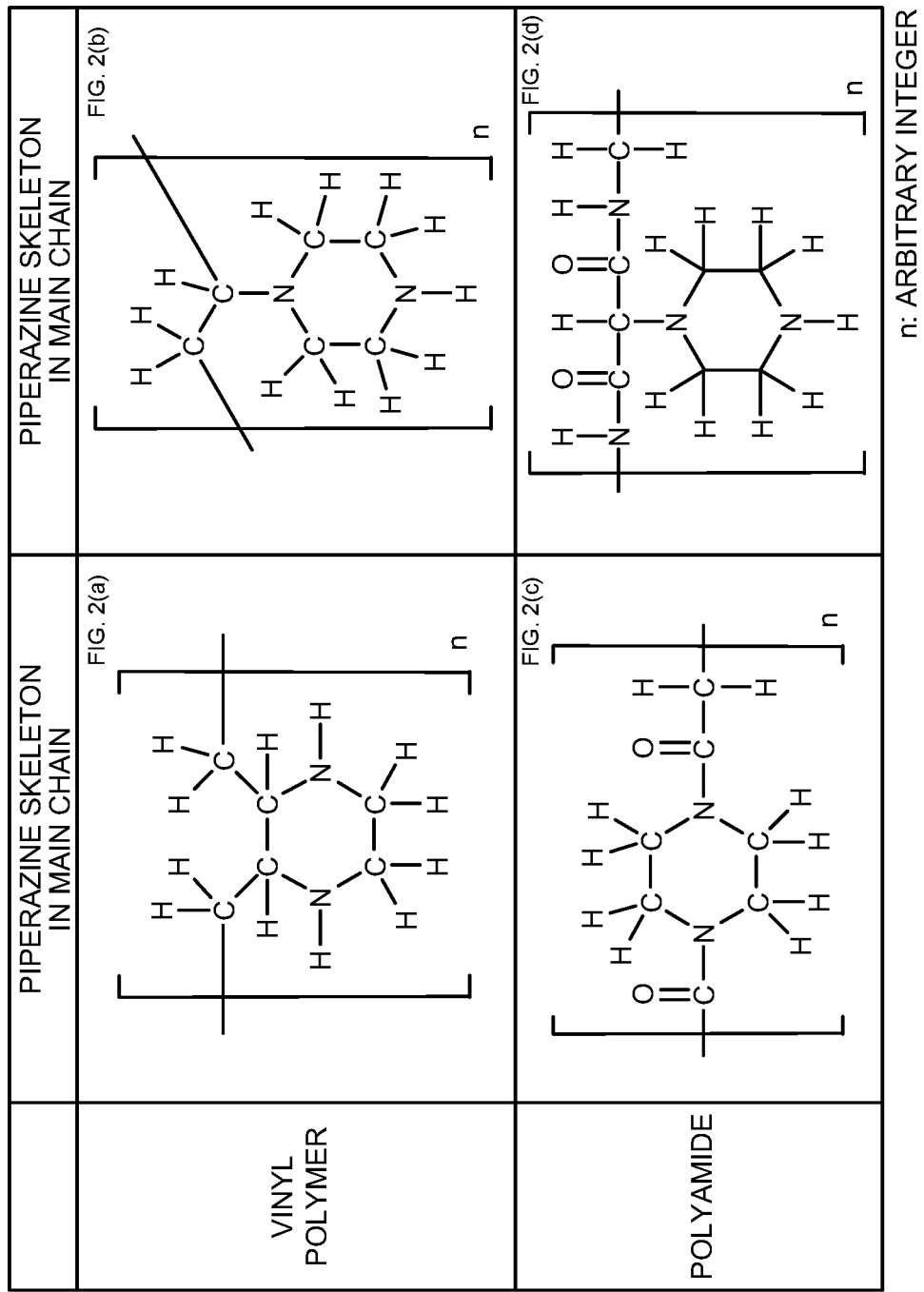

AFTER 42 HOURS → AFTER 311 HOURS

CERIUM OXIDE NANOPARTICLE, DECOMPOSITION METHOD OF NUCLEIC ACID, DECOMPOSITION METHOD OF POLYPEPTIDE, METHOD OF PRODUCING CERIUM OXIDE NANOPARTICLE, OXIDIZING AGENT, ANTIOXIDANT, ANTIFUNGAL AGENT, AND ANTI-VIRUS AGENT

TECHNICAL FIELD

This disclosure relates to a cerium oxide nanoparticle whose surface is covered with a polymer, a decomposition method of a nucleic acid or a polypeptide by using the nanoparticle, a method of producing a cerium oxide nanoparticle, an oxidizing agent, an antioxidant, an antifungal agent, and an anti-virus agent.

BACKGROUND

Under the circumstances of an increase in concerns to safety and hygiene management in recent years, an antibacterial technology to decompose harmful substances and microorganisms is receiving an attention. For example, titanium oxide generates an active oxygen species due to the photocatalytic property thereof. Thus, this has a characteristic to oxidatively decompose an organic substance. Therefore, titanium oxide is expected to be used, besides the use as an antibacterial agent, also for decomposition of low-molecular weight substances such as acetaldehyde and ammonia, as well as various harmful substances such as allergens and viruses.

On the other hand, a cerium oxide nanoparticle (nanoceria) has various characteristics such as an oxidative action, an anti-oxidative action, and an antimicrobial action. It is also known that this has a catalytic activity similar to such enzymes as a catalase, an oxidase, a peroxidase, a superoxide dismutase, and a phosphatase. In addition, it is expected that the cerium oxide nanoparticle may be used differently from the titanium oxide that has photocatalytic characteristics.

On the other hand, in general, nanoparticles tend to readily aggregate. Because the cerium oxide nanoparticle, too, can readily aggregate, this is sometimes used by coating the particle surface thereof by a polymer or the like to enhance dispersibility of the particle. Then, this is occasionally used as an oxidizing agent, an antibacterial agent and the like.

In A. Asati, Angew. Chem. Int. Ed. 2009, 48, 2308-2312 and M. H. Kuchma, Nanomedicine: Nanotechnology, Biology, and Medicine 2010, 6, 738-744, the cerium oxide nanoparticle whose surface is covered with polyacrylic acid or dextran is described, and the oxidation activity and antibacterial activity thereof, among others, are studied.

In Q. Wang, International Journal of Nanomedicine 2013, 8, 3395-3399, the cerium oxide nanoparticle whose surface is covered with, in place of a polymer, sodium bis(2-ethylhexyl) sulfosuccinate is described; and in addition, the phosphatase activity thereof is studied. Q. Wang, International Journal of Nanomedicine discloses that the cerium oxide nanoparticle had the phosphatase activity to hydrolyze a phosphate ester but this failed to decompose a nucleic acid.

We studied a novel use of a cerium oxide nanoparticle whose surface is covered with a polymer. Our study was carried out with regard to decomposition of a plasmid and a polypeptide by using the cerium oxide nanoparticle whose surface is covered with the polyacrylic acid described in A. Asati, Angew. Chem. Int. Ed.; but the decomposition of the plasmid was not able to be recognized, namely the same result as reported in Q. Wang, International Journal of Nanomedicine was obtained. We also found that the decomposition rate of the polypeptide was very low.

We therefore found the need to find a novel cerium oxide nanoparticle that can decompose a nucleic acid and a polypeptide with high decomposition rates.

SUMMARY

We then found that the cerium oxide nanoparticle whose surface is covered with a vinyl polymer having a skeleton of piperazine, pyridine, imidazole, or carbazole or with a polyamide having a skeleton of piperazine, pyridine, imidazole, or carbazole is able to decompose a nucleic acid and a polypeptide with high decomposition rates.

We thus provide:

(1) A cerium oxide nanoparticle, a surface of the cerium oxide nanoparticle being covered with a vinyl polymer having a heterocyclic amine skeleton or with a polyamide having a heterocyclic amine skeleton.
(2) The cerium oxide nanoparticle according to (1), wherein the heterocyclic amine skeleton is formed of any of piperazine, pyridine, imidazole, or carbazole.
(3) The cerium oxide nanoparticle according to (1), wherein the vinyl polymer is a polymer having the heterocyclic amine skeleton in a side chain of the vinyl polymer.
(4) The cerium oxide nanoparticle according to (1), wherein the polyamide is a polymer having the heterocyclic amine skeleton in a main chain of the polyamide.
(5) The cerium oxide nanoparticle according to any one of (1) to (4), wherein a Ce L3 edge XANES spectrum obtained by an X-ray absorption fine structure spectrometry measurement has a maximum absorption in a range of 5726.0 eV to 5729.0 eV and in a range of 5735.0 eV to 5739.0 eV.
(6) A decomposition method of a nucleic acid, including causing a sample including the nucleic acid to contact with the cerium oxide nanoparticle according to any one of (1) to (5).
(7) A decomposition method of a polypeptide, including causing a sample including the polypeptide to contact with the cerium oxide nanoparticle according to any one of (1) to (5).
(8) A method of producing a cerium oxide nanoparticle whose surface is covered with a polymer, the method including:
  process a: mixing a solution of a polymer having a heterocyclic amine skeleton with a solution including a cerium (III) ion or with a cerium (III) salt to obtain a mixed solution; and
  process b: adding an oxidizing agent to the mixed solution obtained at the process a.
(9) An oxidizing agent comprising the cerium oxide nanoparticle according to any one of (1) to (5).
(10) An antioxidant comprising the cerium oxide nanoparticle according to any one of (1) to (5).
(11) An antifungal agent comprising the cerium oxide nanoparticle according to any one of (1) to (5).
(12) An anti-virus agent comprising the cerium oxide nanoparticle according to any one of (1) to (5).

The cerium oxide nanoparticle can decompose a nucleic acid and a polypeptide with much higher decomposition rates than conventional nanoparticles.

BRIEF DESCRIPTION OF THE DRAWINGS

FIGS. 2(a)-2(d) are diagrams in a table format showing the structures of four polymers containing piperazine skeletons.

DETAILED DESCRIPTION

The cerium oxide nanoparticle whose surface is covered with a vinyl polymer having a heterocyclic amine skeleton or with a polyamide having a heterocyclic amine skeleton is sometimes described in this specification as the cerium oxide nanoparticle.

Figure 1A:
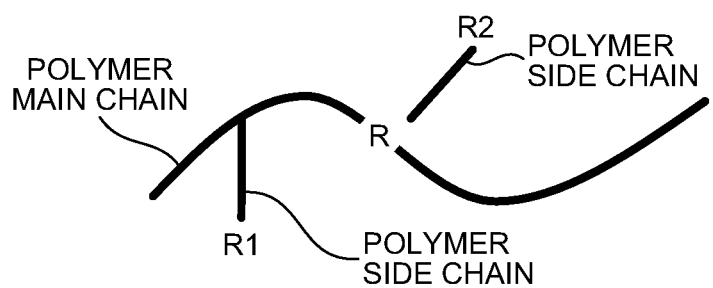
FIGS. 1(a)-1(c) are drawings to explain the structures of the polymers used.
Figure 1B:
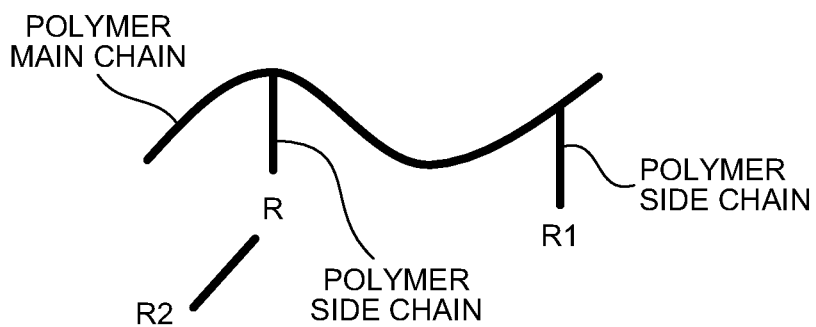
Figure 1C:
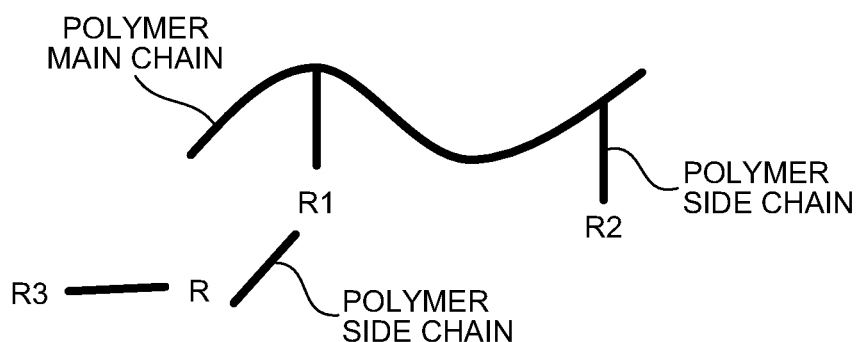

As illustrated in FIG. 1, the vinyl polymer or the polyamide to be used has a heterocyclic amine skeleton R such as piperazine, pyridine, imidazole, or a carbazole in a main chain thereof (FIG. 1(a)) or in a side chain thereof (FIGS. 1(b) and 1(c)). The vinyl polymer or the polyamide may have a substituent group in an arbitrary position in the main chain or in the side chain, or in an arbitrary position in the heterocyclic amine skeleton such as piperazine, pyridine, imidazole, or carbazole. The polymer illustrated in FIG. 1(a) has the heterocyclic amine skeleton in the main chain, and has the substituent groups R1 and R2 in the side chain. The polymer illustrated in FIG. 1(b) has the heterocyclic amine skeleton in the side chain, and has the substituent group R2 as the substituent group of the heterocyclic amine skeleton. The polymer illustrated in FIG. 1(c) has the heterocyclic amine skeleton in the side chain, in which the heterocyclic amine skeleton is the substituent group of the substituent group R1 in the side chain, and has the substituent group R3 as the substituent group of the heterocyclic amine skeleton. The structures illustrated in FIGS. 1(a) to 1(c) are mere examples of the vinyl polymer or the polyamide to be used; they are not limited to these structures. Unless otherwise specifically mentioned, the substituent groups are an alkyl group, an acetyl group, a hydroxy group, an amino group, a cyano group, a carboxy group, an ester group, an aldehyde group, an amide group, an ether group, a ketone group, a halogen group, a sulfonate group, or a phosphate group. The substituent group may be single or plural.

The vinyl polymer has a methylene group in the main chain thereof. Examples of the structure of the vinyl polymer having a piperazine skeleton in the main chain or in the side chain include FIGS. 2(a) and 2(b). As illustrated in FIG. 2(a), when the piperazine skeleton is present in the main chain, the piperazine skeleton is present between the methylene group and the methylene group in the main chain. When the main chain has other heterocyclic amine skeleton such as a skeleton of pyridine, imidazole, or carbazole, the heterocyclic amine skeleton is present between the methylene group and the methylene group, similarly to FIG. 2(a).

When the vinyl polymer has the piperazine skeleton in the side chain thereof, the piperazine skeleton may be bonded directly to the carbon atom in the methylene group as illustrated in FIG. 2(b), or the piperazine skeleton may be bonded via an alkyl group or an amino group. When the vinyl polymer has other heterocyclic amine skeleton such as a skeleton of pyridine, imidazole, or carbazole, the heterocyclic amine skeleton such as the skeleton of pyridine, imidazole, or carbazole may be bonded directly to the carbon atom of the methylene group similarly to FIG. 2(b), or may be bonded via the alkyl group or the amino group.

The vinyl polymer is preferably the vinyl polymer having the skeleton of piperazine, pyridine, imidazole, or carbazole in the side chain thereof. The vinyl polymer having the skeleton of piperazine, pyridine, imidazole, or carbazole in the side chain thereof may be obtained by a polymerization reaction of a vinyl monomer having a vinyl group.

Illustrative examples of the vinyl monomer include specifically 1-vinyl piperazine, (4-vinylpiperazin-1-yl)methane amine, 2-(4-vinylpiperazin-1-yl)ethane-1-amine, 2-vinyl piperazine, (3-vinylpiperazin-1-yl)methane amine, 2-(3-vinylpiperazin-1-yl)ethane-1-amine, (2-vinylpiperazin-1-yl) methane amine, 2-(2-vinylpiperazin-1-yl)ethane-1-amine, 2-vinyl pyridine, 3-vinyl pyridine, 4-vinyl pyridine, 1-vinyl imidazole, 2-vinyl imidazole, 4-vinyl imidazole, and 9-vinyl carbazole. The vinyl monomer may have a substituent group in an arbitrary position other than the vinyl group; the vinyl group may have a methyl group or a cyano group as the substituent group.

The vinyl polymer may be a homopolymer or a copolymer produced from raw materials of two or more vinyl monomers.

Examples of the vinyl polymer that can be preferably used are specifically poly(1-vinylpiperazine), poly((4-vinylpiperazin-1-yl)methaneamine), poly(2-(4-vinylpiperazin-1-yl) ethane-1-amine), poly(2-vinylpyridine), poly(3-vinylpyridine), poly(4-vinylpyridine), poly(1-vinylimidazole), poly (2-vinylimidazole), poly(4-vinylimidazole), and poly(9-vinylcarbazole).

The polyamide is the polymer having an amide bond in the main chain thereof. As illustrated in FIG. 2(c), when the main chain has the piperazine skeleton, the piperazine skeleton exists between the carbonyl group and the carbonyl group in the main chain, and the nitrogen atoms in the heterocyclic ring of the piperazine skeleton form the amide bonds with the carbonyl groups. When the main chain has other heterocyclic amine skeleton such as the skeleton of pyridine, imidazole, or carbazole having two or more primary or secondary amino groups, the heterocyclic amine skeleton exists between the carbonyl group and the carbonyl group, similarly to FIG. 2(c).

When the polyamide has the piperazine skeleton, the piperazine skeleton may be bonded directly to the carbon atom that connects the amide bonds as illustrated in FIG. 2(d), or the piperazine skeleton may be bonded via an alkyl group or an amino group. When the polyamide has other heterocyclic amine skeleton such as the skeleton of pyridine, imidazole, or carbazole, the heterocyclic amine skeleton such as the skeleton of pyridine, imidazole, or carbazole may be bonded directly to the carbon atom that connects the amide groups similarly to FIG. 2(d), or may be bonded via the alkyl group or the amino group.

The polyamide is preferably the polymer having the piperazine skeleton in the main chain or in the side chain thereof, while more preferably the polymer having the piperazine skeleton in the main chain, as illustrated in FIG. 2(c).

The polyamide having the piperazine skeleton in the main chain may be obtained by a polycondensation reaction between an amine having the piperazine skeleton and a dicarboxylic acid.

Illustrative examples of the preferable amine having the piperazine skeleton include piperazine, (aminomethyl) piperazine, (aminoethyl) piperazine, (aminopropyl) piperazine, (aminobutyl) piperazine, 1,4-bis(aminomethyl) piperazine, 1,4-bis(2-aminoethyl) piperazine, 1,4-bis(3-aminopropyl) piperazine, and 1,4-bis(4-aminobutyl) piperazine. Among these, (aminoethyl) piperazine and 1,4-bis(3-aminopropyl) piperazine are more preferable. These amines may have a substituent group in an arbitrary position other than the position of the nitrogen atom capable of forming the amide bond.

Illustrative example of the preferable dicarboxylic acid include 1H-imidazole-2,4-dicarboxylic acid, 1H-imidazole-2,5-dicarboxylic acid, 1H-imidazole-4,5-dicarboxylic acid, pyridine-2,3-dicarboxylic acid, pyridine-2,4-dicarboxylic acid, pyridine-2,5-dicarboxylic acid, pyridine-2,6-dicarboxylic acid, pyridine-3,4-dicarboxylic acid, pyridine-3,5-dicarboxylic acid, adipic acid, sebacic acid, dodecadicarboxylic acid, terephthalic acid, and isophthalic acid. These dicarboxylic acids may have a substituent group in an arbitrary position other than the carboxy group that can form the amide bond.

The polyamide is preferably those obtained from the amines and dicarboxylic acids described above in any combinations thereof, and especially preferably the polyamide obtained from a combination of (aminoethyl) piperazine and adipic acid.

The polyamide may have a polyalkylene glycol structure in the main chain thereof. Examples of such polyamide include specifically the polyamide having the skeletons of (aminoethyl) piperazine, adipic acid, and bis(aminopropyl) polyethylene glycol.

The polyamide of the polyamide having the heterocyclic amine skeleton such as piperazine, pyridine, imidazole, or carbazole with other polymer, or a copolymer of the polyamide with other polymer. In this example, illustrative examples of the other polymer include specifically polycaproamide (nylon 6), polyhexamethylene adipamide (nylon 66), polytetramethylene adipamide (nylon 46), polypentamethylene adipamide (nylon 56), polypentamethylene sebacamide (nylon 510), polyhexamethylene sebacamide (nylon 610), polyhexamethylene dodecamide (nylon 612), a polyhexamethylene adipamide/polyhexamethylene terephthalamide copolymer (nylon 66/6T), a polyhexamethylene adipamide/polyhexamethylene terephthalamide/polyhexamethylene isophthalamide copolymer (nylon 66/6T/61), a polyhexamethylene terephthalamide/polyhexamethylene isophthalamide copolymer (nylon 6T/61), and polyxylene adipamide (nylon XD6).

The molecular weight of the vinyl polymer or of the polyamide may be 3,000 to 1,000,000, and this is preferably 10,000 to 50,000.

The cerium oxide nanoparticle has the structure having in the center thereof the cerium oxide particle formed of a mixture of $Ce_2O_3$ and $CeO_2$ (sometimes described as a center nucleus), and has the surface thereof covered with the afore-mentioned polymer. The particle diameter of the center nucleus may be about 1 nm or more and 100 nm or less. The particle diameter is obtained such that at least two or more of a long-axis diameter, a short-axis diameter, and a unidirectional diameter are measured by using a transmission electron microscope followed by calculating the average value of them.

The ratio of $Ce_2O_3$ to $CeO_2$ in the center nucleus can be calculated as the ratio of cerium (III) to cerium (IV). The ratio may be calculated by using an X-ray photoelectron spectrometry (XPS) method after the cerium oxide nanoparticle is dried. The energy states of cerium (III) and cerium (IV) in $Ce_2O_3$ and $CeO_2$ may be observed by measurement of the X-ray absorption fine structure (XAFS) spectrum. In the XAFS spectrum, the structure at about 20 eV from the absorption edge is called XANES (X-ray absorption near edge structure), and the extended X-ray absorption fine structure appearing at more than about 100 eV in a high-energy side from the absorption edge is called EXAFS (extended X-ray absorption fine structure). From XANES, information relating to the valency and structure of the focused atom can be obtained; in the EXAFS analysis, information relating to the local structure of the sample, as well as the atom species, valency, and distance around the focused atom can be obtained by Fourier transformation of the actual spectrum (corresponding to FT-EXAFS/radial distribution function). The energy state of cerium (III) and cerium (IV) in the oxidation reduction reaction of cerium oxide is reflected in the peak position and peak intensity ratio of the maximum absorption in the XANES spectrum.

Preferably, the Ce L3 edge XANES spectrum obtained by measurement of the X-ray absorption fine structure spectrum has the maximum absorptions of 5,726.0 to 5,729.0 eV and 5,735.0 to 5,739.0 eV.

In the cerium oxide nanoparticle, the particle diameter including the polymer layer on the surface thereof is preferably 200 nm or less, as the hydrodynamic diameter. The hydrodynamic diameter is calculated as follows. The cerium oxide nanoparticles are dissolved in an arbitrary solvent such as water, ethanol, or pyridine. Then, the dynamic light scattering thereof is measured to obtain the autocorrelation function; this is then analyzed by the Marquadt method to calculate from the number conversion histogram the average particle diameter as the hydrodynamic diameter. Measurement of the dynamic light scattering is done by using ELS-Z manufactured by Otsuka Electronics Co., Ltd.

The cerium oxide nanoparticle may be produced by the method of producing the cerium oxide nanoparticle that includes: the process a at which a solution of the polymer having the heterocyclic amine skeleton such as piperazine, pyridine, imidazole, or carbazole is mixed with a solution including a cerium ion (III) or with a cerium (III) salt to obtain a mixed solution; and the process b at which an oxidizing agent is added to the mixed solution obtained at the process a. Hereinafter, the method of producing the cerium oxide nanoparticle will be explained along these processes separately.

At the process a, a solution of the polymer having the heterocyclic amine skeleton such as piperazine, pyridine, imidazole, or carbazole is mixed with a solution including a cerium ion (III) or with a cerium (III) salt to obtain a mixed solution. The polymer solution to be used at the process a may be prepared by dissolving the polymer into an arbitrary solvent. The solvent is preferably water or a solvent that is soluble in water is preferable. Illustrative examples of the water-soluble solvent include specifically methanol, ethanol, propanol, butanol, tetrahydrofuran, glycerol, ethylene glycol, acetone, dimethylformamide (DMF), dimethyl sulfoxide (DMSO), triethylamine, and pyridine. Polyamide and polyvinyl imidazole are preferably soluble in water; poly(4-vinylpyridine) and poly(2-vinylpyridine) are preferably soluble in an aqueous 80% ethanol solution; and polyvinyl carbazole is preferably soluble in pyridine. When these polymers are not readily dissolved, they may be dissolved by heating or by an ultrasonic treatment.

The concentration of the polymer solution is preferably 0.01% or more and 5% or less, while more preferably 0.1% or more and 2% or less, in terms of the mass concentration.

Mixing of the polymer solution with the solution including the cerium (III) ion or with the cerium (III) salt may be effected by mixing the polymer solution with the solution including the cerium (III) ion after these solutions were prepared separately in advance; or alternatively, when the solvent of the polymer solution is water or a water-soluble solvent, the cerium (III) salt may be added into the polymer solution for mixing. The solution including the cerium (III) ion may be prepared by dissolving the cerium (III) salt into an arbitrary solvent. Examples of the cerium (III) salt include cerium (III) nitrate hexahydrate.

When the cerium (III) nitrate hexahydrate is used as the cerium (III) salt, the mass ratio of the cerium (III) nitrate hexahydrate to the polymer upon mixing is preferably 0.1 or more and 5.0 or less. The resulting mixture solution is preferably mixed for 5 minutes or longer until the solution becomes uniform.

At the process b, an oxidizing agent is added into the mixed solution obtained at the process a. Illustrative examples of the oxidizing agent to be used at the process b include nitric acid, potassium nitrate, hypochlorous acid, chlorous acid, chloric acid, perchloric acid, halogens, hydrogen halides, permanganate salts, chromic acid, dichromic acid, oxalic acid, hydrogen sulfide, sulfur dioxide, sodium thiosulfate, sulfuric acid, and hydrogen peroxide. Among these, hydrogen peroxide is especially preferable. The addition amount thereof may be 0.1 equivalent or more and 10 equivalents or less relative to the cerium (III) ion as molar equivalent; the addition amount is preferably 1 equivalent or more and 2 equivalents or less.

When the oxidizing agent is added to the mixed solution obtained at the process a, the cerium (III) ion is oxidized to cerium (IV). Then, the particle formation reaction starts to give the cerium oxide particle that is formed of a mixture of $Ce_2O_3$ and $CeO_2$ in the center thereof whose surface is covered with the polymer. Upon addition of the oxidizing agent into the mixed solution of the polymer with the cerium (III) ion, the formation reaction to produce the cerium oxide nanoparticle starts. During this reaction, the solution is colored to yellow, orange, red, brown, or the like. This coloring takes place because the cerium (III) ion changes to cerium (IV), in which the coloring degree is determined by the ratio of cerium (III) to cerium (IV) that are present in the surface of the cerium oxide nanoparticle. Termination of the reaction can be judged at the time when the color does not change any further. The reaction usually terminates in about 30 minutes to 1 hour.

For example, 100 µL of the aqueous solution of 10 wt % of cerium (III) nitrate hexahydrate is mixed with 5 mL of the aqueous solution of 0.1 wt % of polyvinyl imidazole, which is then followed by addition of 100 µL of the aqueous solution of 1.2 wt % of hydrogen peroxide. Then, upon heating the resulting solution to 40° C., the color of the solution changes at first to yellow. Then, the yellow color gradually deepens thereby finally resulting in an orange color, indicating termination of the reaction.

The size of the cerium oxide nanoparticle may be controlled by concentration of the polymer solution. The polymer solution with a higher concentration gives the particle having a larger particle diameter; the polymer solution with a lower concentration gives the particle with a smaller particle diameter.

Other than this, the size of the cerium oxide nanoparticle may be controlled by the reaction temperature as well. When the reaction temperature is made equal to or higher than the glass transition temperature (Tg) of the polymer, the particle having a large particle diameter may be obtained; when the reaction temperature is made lower than Tg, the particle with a small particle diameter may be obtained. The reaction temperature may be arbitrarily set in the range of 4 to 95° C.

The cerium oxide nanoparticle may be stored in the solution after termination of the reaction; or this may be stored in the dry state after the cerium oxide nanoparticle is taken out from the solution after termination of the reaction. When this is stored in the solution, this is stored preferably in a refrigerated state. When the cerium oxide nanoparticle is dried, this may be done as described below. For example, the solution after termination of the reaction is filtrated by an ultrafiltration membrane or dialyzed by a semitransparent membrane to remove the unreacted oxidizing agent, the cerium (III) ion, and the excess polymer, these being remained in the solution after termination of the reaction. Then, this is dried by using an evaporator, a freeze dryer or the like.

When the cerium oxide nanoparticle is used, a nucleic acid and a polypeptide can be decomposed. For example, there is a possibility to decompose a virus, which includes the nucleic acid and the polypeptide as the main components therein. Also, there is a possibility to decompose an allergen, which includes the polypeptide as the main component therein.

To decompose the nucleic acid means that a nucleotide chain that constitutes the nucleic acid is cleaved. When the nucleic acid is decomposed, a steric structure of the nucleic acid changes, or the nucleic acid is fragmented. For example, in a cyclic double-chained nucleic acid such as a plasmid, when the nucleic acid is in the uncleaved state, this has a closed circular structure; when one of the two chains is cleaved, this has an open circular structure; and when both of the two chains are cleaved, this has a linear structure.

To decompose the polypeptide means that a polypeptide chain is cleaved thereby resulting in the change of the steric structure of the polypeptide or in fragmentation of the polypeptide.

Decomposition of the nucleic acid or the polypeptide by using the cerium oxide nanoparticle may be effected by contacting under the dry state thereof with a sample that includes the nucleic acid or the polypeptide; or by contacting, as the solution that includes the cerium oxide nanoparticle, the solution after termination of the reaction as it is with the sample that includes the nucleic acid or the polypeptide. With regard to the contacting method, when the sample that includes the nucleic acid and the polypeptide is a liquid, the contact may be effected by adding and mixing this sample with the cerium oxide nanoparticle or with the solution that includes the cerium oxide nanoparticle. Also, the contact of the solution that includes the cerium oxide nanoparticle with the sample such as a virus that includes the nucleic acid or the polypeptide and that is staying in an air may be effected by scattering this solution into an air as a mist. Alternatively, the cerium oxide nanoparticle is kneaded as an additive into a textile, a tube, a bead, a rubber, a film, a plastic or the like, or is applied onto the surface of these materials. Then, this may be contacted with the sample that includes the nucleic acid or the polypeptide. The solution that includes the cerium oxide nanoparticle may be prepared by mixing this nanoparticle with water or an arbitrary solution.

There is no particular restriction in the nucleic acid that can be decomposed by the cerium oxide nanoparticle so far as the nucleic acid is those having nucleotides polymerized linearly or circularly. Thus, this may also be an artificial nucleic acid. Illustrative examples of the nucleic acid include RNA, DNA, and RNA/DNA (chimera). Illustrative examples of the DNA include cDNA, micro DNA (miDNA), plasmid DNA, genome DNA, synthetic DNA, cell-free DNA (cfDNA), ctDNA, and mitochondria DNA (mtDNA). Illustrative examples of the RNA include total RNA, mRNA, rRNA, miRNA, siRNA, snoRNA, snRNA, non-coding RNA, precursors of these RNAs, and synthetic RNAs. Synthetic DNA and synthetic RNA are those prepared artificially, for example, by using an automatic nucleic acid synthesizing apparatus on the basis of a prescribed nucleotide sequence (any of a natural sequence and a non-natural sequence may be used). Illustrative examples of the artificial nucleic acid include LNA and BNA. For decomposition, an arbitrary sample including these nucleic acids may be used.

Illustrative examples of the polypeptide that can be decomposed by the cerium oxide nanoparticle include a protein and a polypeptide that is artificially synthesized on the basis of a prescribed amino acid sequence (any of a natural sequence and a non-natural sequence may be used). A polypeptide nucleic acid (PNA) having a nucleic acid-like structure that retains a polypeptide structure in the main chain thereof, a virus whose main components are a protein and a nucleic acid, and the like may also be used as the sample that includes the nucleic acid or the polypeptide.

Illustrative examples of the method to confirm decomposition of the nucleic acid include: electrophoreses such as an acrylamide gel electrophoresis, an agarose gel electrophoresis, and a capillary electrophoresis; and nucleic acid analysis methods by using a size exclusion chromatography, a mass-spectrometry analysis and the like. When the nucleic acid is decomposed, the decrease in the target band concentration or the target peak intensity as compared with those before the decomposition, or the disappearance of the band or of the peak or the like may be confirmed. Also, the decomposition may be confirmed by emergence of a new band or peak that indicates presence of a small fragment as compared with those before the decomposition. Specifically, when the cyclic double-chain nucleic acid is decomposed, the closed circular structure, the open circular structure, and the linear structure can be confirmed as the independent bands by the electrophoresis. Also, when the steric structure of the nucleic acid is changed by decomposition, after the electrophoresis, there is an instance when the position of the band shifts from the position before the decomposition.

The decomposition of the polypeptide may be confirmed by the method similar to that used for confirmation of decomposition of the nucleic acid as described above.

The decomposition rate of the nucleic acid or of the polypeptide may be calculated by the method described below. First, "Sample" that is obtained by contacting the sample that includes the nucleic acid or the polypeptide with the cerium oxide nanoparticle is prepared (the sample that is obtained by this contact is sometimes called "Sample"). For the control bands, the sample that includes the nucleic acid or the polypeptide not contacted with the cerium oxide nanoparticle. The Sample having been contacted with the cerium oxide nanoparticle and the control are analyzed by the electrophoresis, the size exclusion chromatography, or the like as described before. In using the electrophoresis, the control and the Sample are subjected to the electrophoresis. Then, after the band concentrations at the same position are confirmed, each band concentration is expressed by the corresponding numerical value. The band concentration of the control is expressed by (X), the band concentration of the Sample is expressed by (Y); and then, the ratio of the difference between (X) and (Y) to (X) is defined as the decomposition rate. When the cerium oxide nanoparticle is contacted with the sample that includes the nucleic acid or the polypeptide, if the nucleic acid or the polypeptide are adsorbed to the cerium oxide nanoparticle, the nucleic acid or the polypeptide may be recovered by eluting these by using an arbitrary eluting solution. Illustrative examples of the eluting solution usable include the citrate buffer including citric acid and sodium citrate, the phosphate buffer including phosphoric acid and sodium phosphate, and the Tris-EDTA buffer that is obtained by adding EDTA to the Tris-hydrochloric acid buffer, which includes trishydroxy amino methane and hydrochloric acid.

The cerium oxide nanoparticle may be used as an oxidizing agent. For example, by utilizing the oxidative action of the cerium oxide nanoparticle, this may be used in an organic synthetic reaction, a polymer polymerization, and wet-etching of a semiconductor. By utilizing the oxidative action, this may be used as a substitute substance of an oxidative enzyme. Specifically, this may be used as a substitute of an oxidase or a peroxidase, in a detection reaction or a tissue dying using an antibody-antigen reaction or a nucleic acid hybridization, or in an electrochemical detection reaction by immobilizing this to an electrode. The performance of this as the oxidizing agent described above may be evaluated by the measurement method of the oxidase activity, the measurement method of the peroxidase activity or the like, which will be described later. In addition to these, by utilizing the oxidative action thereof, this may be used for decomposition and removal of dirt, smell, and an allergen as a bleaching agent or as a disinfectant. Specifically, as the bleaching agent, this may be used for cleaning of cloth, tableware, a kitchen, a toilet, a washroom, a bathroom, medical equipment and so forth. Also, this may be added as the disinfectant to a swimming pool, a bathtub, and a hot spring; and furthermore, this may be used as a body soap, a hand cleaning material, a disinfecting medicine, a gargle, a mouth washer and so forth. The performance of this as the oxidizing agent described above may be evaluated by the color fading reaction of an organic dye or the like, which will be described later.

The color fading reaction of the organic dye can also be used for evaluation of the photocatalytic performance of titanium oxide. The decomposition rate of the dye thereby obtained can be used as the indicator of the characteristic with regard to the oxidative decomposition of an organic substance. Specifically, the decomposition rate of the dye is calculated as follows. First, the solution of the cerium oxide nanoparticle is mixed with an organic dye such as Acid Orange 7 (AO7). Then, the resulting mixed solution is allowed to statically leave for a prescribed period. As a control, the AO7 solution not including the cerium oxide nanoparticle is treated similarly. After the reaction, the absorption spectra of all the solutions are measured. For analysis, the absorbance at 485 nm, the maximum absorption wavelength of AO7, is used. The ratio of the difference value between the absorbance of the control (Ic) and the absorbance of the solution including the cerium oxide nanoparticle (I) to the absorbance of the control (Ic) is calculated as the decomposition rate.

The value of the oxidase activity may be obtained by the method such as the one described in A. Asati, Angew. Chem. Int. Ed. 2009, 48, 2308-2312. Specifically, a dilution series is prepared by using the reagent such as TMBZ that is capable of being colored by oxidation; to each of them, the solution of the cerium oxide nanoparticle having the identical concentration is added to carry out the coloring reaction of 3,3',5,5'-tetramethyl benzidine (TMBZ). The Michaelis Menten equation is applied to this reaction to calculate the oxidase activity. From the temporal change of the absorbance in each TMBZ concentration, the reaction rate is calculated. Then, the reciprocal of the reaction rate is plotted against the reciprocal of the concentration of the TMBZ substrate. A straight line is obtained by plotting in each concentration; the maximum reaction rate Vmax is obtained from the reciprocal of the y-intercept; and the Michaelis Menten constant Km is calculated by multiplying this value with the slope of the straight line. The maximum reaction rate Vmax is compared as the value that indicates the oxidase activity. The oxidase activity may be measured as well by using a compound such as 2,2'-azinobis(3-ethylbenzothiazoline-6-sulfonic acid) (AzBTS) or dopamine in place of TMBZ.

The cerium oxide nanoparticle may be used as an antioxidant. The antioxidant means the substance having a reductive property, thereby suppressing excessive oxidation of a lipid or reacting with an active oxygen (superoxide ion, hydroxy radical, hydrogen peroxide or the like) to suppress the action of the active oxygen (Standard Dictionary of Chemical Terms; second edition, Maruzen Publishing Co., Ltd.). For example, by utilizing the anti-oxidative action of the cerium oxide nanoparticle, this may be used as a reducing agent in an organic reaction or as a radical terminating agent in a polymer polymerization. Also, by utilizing the anti-oxidative action thereof, this may be used as a cosmetic to protect a skin from lipid peroxidation and an active oxygen. On top of these, by utilizing the anti-oxidative action thereof, this may be used as the substitute of an anti-oxidative enzyme. Specifically, as a substitute of a catalase, this may be used in a detection reaction of hydrogen peroxide or in an electrochemical detection reaction by immobilizing this to an electrode. In addition, this may be used to neutralize hydrogen peroxide that is used in an industry such as foods, semiconductor, textile, pulp and paper manufacturing, as well as used to sterilize a public bath and to remove slime in a piping. These performances may be evaluated by the catalase activity that will be described later. Furthermore, by utilizing the anti-oxidative action thereof, this may be used as an antioxidant. Specifically, to prevent a rubber, plastics, a fuel, a detergent, a food, an animal feed from deterioration, this may be added to these. The performance as the antioxidant as described above may be evaluated by a scavenging reaction or like of an active species, which will be described later.

Furthermore, the cerium oxide nanoparticle may be used as an antioxidant in a drug to treat an oxidation stress or an inflammation of a human or of an animal. In general, it is considered that the cerium oxide nanoparticle having a catalase activity can be used for prevention and treatment of a disease that relates to the oxidation stress such as an apoplectic stroke, disseminated sclerosis, amyotrophic lateral sclerosis, and ischemia reperfusion damage by administering to a test object by a topical, an enteral, or a parenterally method such as injection, drip infusion, or transplantation. Also, it is considered that the cerium oxide nanoparticle having a catalase activity can reduce an inflammation topically or systemically when this is held on the surface of an artificial organ represented by a dialysis membrane and medicinal equipment such as a cannula, a catheter, and a stent.

The scavenging reaction of an active species may be measured as a dye retention rate by the method such as the one described by Y. Xue, J. Phys. Chem. C, 2011, 115, 4433-4438. Specifically, a hydroxy radical is generated by a Fenton reaction by mixing an aqueous iron (II) chloride solution with an aqueous hydrogen peroxide solution. Then, to this solution is added the solution of the cerium oxide nanoparticle to carry out the radical scavenging reaction. This mixture solution is mixed with an organic dye such as a methylene blue. Then, the resulting mixture is allowed to statically leave for a prescribed period. As a control, the same treatment is carried out to the solution not including the cerium oxide nanoparticle. Furthermore, the methylene blue solution having the same concentration as the reaction solution is prepared as the standard solution. Then, the absorption spectra of these solutions are measured. For the analysis, the absorbance at 664 nm, the wavelength of the maximum absorption of the methylene blue, is used. The difference ($\Delta I_0$) between the absorbance ($I_0$) of the standard solution and the absorbance ($I_c$) of the control, and the difference ($\Delta I$) between the absorbance (I) of the solution including the cerium oxide nanoparticle and the absorbance ($I_c$) of the control are calculated. The ratio of the latter ($\Delta I$) to the former ($\Delta I_0$) is calculated as the decomposition rate; and this is taken as the dye retention rate. This value indicates the radical scavenging performance. The dye retention rate may be obtained by using a methyl violet in place of the methylene blue.

The value of the catalase activity may be obtained in accordance with the protocol by using Amplex Red Catalase Assay Kit (A22180) (manufactured by Thermo Fisher Scientific Inc.) as described in Japanese Patent Application Laid-open Publication No. 2018-508568. The Reaction Buffer included in the kit, the cerium oxide nanoparticle, and the aqueous hydrogen peroxide solution are mixed. Then, the resulting mixture is allowed to statically leave for 30 minutes to carry out the decomposition reaction of hydrogen peroxide. The reaction solution is passed through the 30 kD ultrafiltration membrane. Then, the flow-through solution is mixed with Working Solution included in the kit to carry out the reaction at 37° C. for 30 minutes. The resorufin generated by the reaction is excited at 544 nm, and the fluorescence intensity at 590 nm is measured. By comparison with the calibration curve of the catalase standard whose active value has already been known, in which this standard is included in the kit, the catalase activity of the cerium oxide nanoparticle is calculated. For measurement of the catalase activity, other kits such as EnzyChrom Catalase Assay Kit manufactured by BioAssay Systems, LLC may also be used.

The cerium oxide nanoparticle may be used as an antifungal agent. Illustrative examples of the method to evaluate the antifungal performance include: the method in which a suspension solution of a mold's spore is mixed with the test solution followed by culturing in an inorganic salt agar medium or a glucose-including inorganic salt agar medium to observe the growing state thereof; the method in which the test solution is added to an agar medium to observe the growth suppression; and the method in which the test solution is added to an agar medium to measure the growth-suppression circle. The method in which the test solution is added to an agar medium to observe the growth suppression and the method in which the test solution is added to an agar medium to measure the growth-suppression circle are preferably used.

Illustrative examples of the mold that can be inactivated by the cerium oxide nanoparticle include *Penicillium, Aspergillus, Alternaria, Cladosporium, Trichoderma*, and *Chaetomium*.

When the cerium oxide nanoparticle is used as the antifungal agent, this is kneaded as an additive into a textile, a tube, a bead, a rubber, a film, a plastic, or the like, or is applied onto the surface of these materials. Illustrative examples of the processed products like these include a *Chrysanthemum*-shaped cover of the drain hole in a kitchen sink, a drain plug, a fixing packing material of a window, a fixing packing material of a mirror, a water-proof packing material in a bathroom, in a washing stand, and in a kitchen, an inner packing material of a refrigerator door, a bath mat, an anti-sliding rubber of a washing bowl and a chair, a hose, a shower head, a packing material used in a water purifier, a plastic product of a water purifier, a packing material used in a cloth washing machine, a plastic product used in a cloth washing machine, an air conditioner filter, a filter of air cleaning equipment, a filter for a vacuum cleaner, a filter for a ventilation fan, a filter for a vehicle, a filter for an air conditioner, a fin of an air conditioner, plastic parts such as a rover of an air conditioner's blowing outlet and a blowing fan, a fin of a car air conditioner, plastic parts such as a rover of a car air conditioner's blowing outlet and a blowing fan, a cloth, a bedding cloth, a net in a screen door, a net for a chicken house, nets such as a mosquito net, a wall paper and a window, a blind, an interior material of a building such as a hospital, an interior material of a train and a car, a seat for a vehicle, a blind, a chair, a sofa, virus-treating equipment, and a construction material in various fields such as a door, a ceiling, a floor, and a window.

The cerium oxide nanoparticle may be used as an anti-virus agent. In the method to evaluate the performance thereof as the anti-virus agent, the cerium oxide nanoparticle is caused to contact with a virus. Then, the amount of the virus after contact is quantified. Illustrative examples of the quantifying method of the virus include: the method in which the virus antigen amount is measured by the ELISA method; the method in which the virus nucleic acid is quantified by PCR; the method in which an infectivity titer is measured by the Plaque method; and the method in which an infectivity titer is measured by the 50% infection amount measurement method. The anti-virus performance is measured preferably by the method in which an infectivity titer is measured by the Plaque method or by the 50% infection amount measurement method. The unit of the virus infectivity titer in the 50% infection amount measurement method is expressed by: TCID50 (tissue culture infectious dose 50) when the object of the test is a cultured cell; EID50 (egg infectious dose 50) when an embryonated egg is used; and LD50 (lethal dose 50) in an animal. In the 50% infection amount measurement method, illustrative examples of the method to calculate the infectivity titer from the obtained data include the Reed-Muench method, the Behrens-Karber method, and the Spearman-Karber method. The Reed-Muench method is used. With regard to the judgement standard of the anti-virus performance, in general, when the logarithmic reduction value of the infectivity titer relative to the infectivity titer before action of the cerium oxide nanoparticle, or to the control not including the cerium oxide nanoparticle is 2.0 or greater, this is judged to be effective in the anti-virus performance.

Illustrative examples of the virus that can be inactivated by the cerium oxide nanoparticle include rhino virus, polio virus, foot and mouth disease virus, rotavirus, norovirus, enterovirus, hepatovirus, astrovirus, sapovirus, hepatitis E virus, influenza A virus, influenza B virus, influenza C virus, parainfluenza virus, mumps virus (epidemic parotitis), measles virus, human metapneumovirus, RS virus, nipah virus, hendra virus, yellow fever virus, dengue virus, Japanese B encephalitis virus, West Nile encephalitis virus, hepatitis B virus, hepatitis C virus, eastern equine encephalitis virus, western equine encephalitis virus, o'nyong'nyong virus, rubella virus, Lassa virus, Junin virus, Machupo virus, Guanarito virus, Sabia virus, Crimean-Congo hemorrhagic fever virus, sandfly virus, hantavirus, Sin Nombre virus, rabies virus, Ebora virus, Marburg virus, bat-borne lyssavirus, human T-cell leukemia virus, human immunodeficiency virus, human corona virus, SARS corona virus, human parvovirus, polyoma virus, human papilloma virus, adenovirus, herpes virus, varicella zoster virus, EB virus, cytomegalovirus, smallpox virus, monkeypox virus, cowpox virus, Molluscipoxvirus, and parapox virus.

When the cerium oxide nanoparticle is used as the anti-virus agent, this is kneaded as an additive into a textile, a tube, a bead, a rubber, a film, a plastic or the like, or is applied onto the surface of these materials. Illustrative examples of the processed products like these include a mask, a medical cap, a medical shoe cover, a filter for an air conditioner, a filter for an air cleaner, a filter for a vacuum cleaner, a filter for a ventilation fan, a filter for a vehicle, a filter for an air conditioner, a fin of an air conditioner, plastic parts such as a rover of an air conditioner's blowing outlet and a blowing fan, a fin of a car air conditioner, plastic parts such as a rover of a car air conditioner's blowing outlet and a blowing fan, a cloth, a bedding cloth, a net in a screen door, a net for a chicken house, nets such as a mosquito net, a wall paper and a window, a blind, an interior material of a building such as a hospital, an interior material of a train and a car, a seat for a vehicle, a blind, a chair, a sofa, virus-treating equipment, and a construction material in various fields such as a door, a ceiling, a floor, and window.

EXAMPLES

Our nanoparticles, methods and agents will be explained more specifically by the following Examples.
Materials and Methods Sodium polyacrylate, poly(4-vinylpyridine), and poly(2-vinylpyride) were purchased from Merck KGaA; poly(l-vinylimidazole) and poly(9-vinylcarbazole) were purchased from Maruzen Petrochemical Co., Ltd.; and cerium (III) nitrate hexahydrate and an aqueous 30 wt % hydrogen peroxide solution were purchased from Fuji Film Wako Pure Chemical Corp.

Other reagents were purchased from Fuji Film Wako Pure Chemical Corp., Tokyo Chemical Industry Co., Ltd., and Sigma-Aldrich Co., LLC; they were used as they were without any further purification.

In the following Examples, the polymer having the structural units of (aminoethyl) piperazine and adipic acid is described as polyamide (1); the polymer having the structural units of (aminoethyl) piperazine, bis(aminopropyl) polyethylene glycol, and adipic acid is described as polyamide (2); and these polymers were prepared by referring to Japanese Patent Application Laid-open No. H11-166121.

A hot plate IKA C-MAG HP4 manufactured by IKA Japan K.K. was used.

The hydrodynamic diameter of the cerium oxide nanoparticles covered with the polymer was measured by using the zeta potential particle measurement system ELS-Z manufactured by Otsuka Electronic Co., Ltd.; and the ratio of cerium (III) to cerium (IV) was measured by using Quantera SXM manufactured by PHI Inc.

The QM9414 strain was obtained from NBRC (NITE Biological Resource Center).

Example 1: Preparation of Cerium Oxide Nanoparticle Whose Surface is Covered with Polyamide (1)

The aqueous solution of 0.1 wt % of polyamide (1) was used as the aqueous solution of the polymer having the piperazine skeleton. To 5 mL of the aqueous solution of 0.1 wt % of polyamide (1) was added 100 µL of the aqueous solution of 10 wt % of cerium (III) nitrate hexahydrate. Then, they were stirred at room temperature for 5 minutes. To this was added 100 µL of the aqueous solution of 1.2 wt % of hydrogen peroxide. Then, the reaction was carried out at 40° C. for 1 hour to obtain a yellow aqueous solution of the cerium oxide nanoparticle whose surface was covered with polyamide (1). This aqueous solution was purified by the 30 kD ultrafiltration membrane to obtain as the solution the cerium oxide nanoparticle whose surface was covered with polyamide (1).

Example 2: Preparation of Cerium Oxide Nanoparticle Whose Surface is Covered with Polyamide (2)

The reaction was carried out under the same condition as Example 1, except that the aqueous solution of 0.1 wt % of polyamide (2) was used as the aqueous solution of the polymer having the piperazine skeleton, to obtain a yellow aqueous solution of the cerium oxide nanoparticle whose surface was covered with polyamide (2). This aqueous solution was purified by the 30 kD ultrafiltration membrane to obtain as the solution the cerium oxide nanoparticle whose surface was covered with polyamide (2).

Example 3: Preparation of Cerium Oxide Nanoparticle Whose Surface is Covered with Poly(1-Vinylimidazole)

The reaction was carried out under the same condition as Example 1, except that the aqueous solution of 0.1 wt % of poly(l-vinylimidazole) was used as the aqueous solution of the polymer having the imidazole skeleton, to obtain an orange aqueous solution of the cerium oxide nanoparticle whose surface was covered with poly(l-vinylimidazole). This aqueous solution was purified by the 30 kD ultrafiltration membrane to obtain as the solution the cerium oxide nanoparticle whose surface was covered with poly(l-vinylimidazole).

Example 4: Preparation of Cerium Oxide Nanoparticle Whose Surface is Covered with Poly(4-Vinylpyridine)

The reaction was carried out under the same condition as Example 1, except that 5 mL of the aqueous ethanol solution of 0.1 wt % of poly(4-vinylpyridine) was used as the aqueous solution of the polymer having a pyridine skeleton, using the aqueous 80% by volume of ethanol solution, to obtain a reddish brown solution of the cerium oxide nanoparticle whose surface was covered with poly(4-vinylpyridine). After this aqueous ethanol solution was diluted by water to 70% by volume, this was purified by the 30 kD ultrafiltration membrane, which was then followed by removal of the solvent by a centrifugal evaporator, then further followed by redissolution into dimethyl sulfoxide to obtain as the solution the cerium oxide nanoparticle whose surface was covered with poly(4-vinylpyridine).

Example 5: Preparation of Cerium Oxide Nanoparticle Whose Surface is Covered with Poly(2-Vinylpyridine)

The reaction was carried out under the same condition as Example 1, except that the aqueous ethanol solution of 0.1 wt % of poly(2-vinylpyridine) was used as the aqueous solution of the polymer having a pyridine skeleton, using the aqueous 80% by volume of ethanol solution, to obtain a brown solution of the cerium oxide nanoparticle whose surface was covered with poly(2-vinylpyridine). After this solution was diluted by water to 70% by volume, this was purified by the 30 kD ultrafiltration membrane, which was then followed by removal of the solvent by a centrifugal evaporator, then further followed by re-dissolution into dimethyl sulfoxide to obtain as the solution the cerium oxide nanoparticle whose surface was covered with poly(2-vinylpyridine).

Example 6: Preparation of Cerium Oxide Nanoparticle Whose Surface is Covered with Poly(9-Vinylcarbazole)

The reaction was carried out under the same condition as Example 1, except that the pyridine solution of 0.1 wt % of poly(9-vinylcarbazole) was used as the aqueous solution of the polymer having the carbazole skeleton, to obtain an orange solution of the cerium oxide nanoparticle whose surface was covered with poly(9-vinylcarbazole). This aqueous solution was centrifuged with 10,000 G for 1 hour to remove the supernatant thereof, which was then followed by re-dissolution into dimethyl sulfoxide (DMSO) to obtain as the solution the cerium oxide nanoparticle whose surface was covered with poly(9-vinylcarbazole).

Comparative Example 1: Preparation of Cerium Oxide Nanoparticle Whose Surface is Covered with Polyacrylic Acid The reaction was carried out under the same condition as Example 1, except that the aqueous solution of 1 wt % of sodium polyacrylate was used as the aqueous polymer solution, to obtain a yellow aqueous solution of the cerium oxide nanoparticle whose surface was covered with sodium polyacrylate. This aqueous solution was purified by the 30 kD ultrafiltration membrane to obtain as the solution the cerium oxide nanoparticle whose surface was covered with polyacrylic acid.

Comparative Example 2

With referring to Japanese Patent Application Laid-open Publication No. 2018-508568, the cerium oxide nanoparticle using citric acid (CA)/ethylenediamine di-succinate trisodium salt (EDDS) as a stabilizer was prepared.

Measurement of Hydrodynamic Diameter of Cerium Oxide Nanoparticle Whose Surface is Covered with Polymer The hydrodynamic diameter of the cerium oxide nanoparticle whose surface was covered with the polymer prepared in each of Examples 1 to 6 was measured by the dynamic light scattering (DLS) method. The used solvents for measurement were: water when polyamide (1), polyamide (2), or poly(l-vinylimidazole) was used as the polymer; ethanol when poly(4-vinylpyridine) or poly(2-vinylpyridine) was used as the polymer; and pyridine when poly(9-vinylcabazole) was used as the polymer. The hydrodynamic diameter was obtained in terms of number conversion. The obtained results are listed in Table 1.

TABLE 1

| Cerium oxide nanoparticle whose surface is covered with polymer | | Hydrodynamic diameter [nm] | $Ce^{4+}/Ce^{3+}$ |
|---|---|---|---|
| Polyamide (1) | Example 1 | 12.6 ± 02.9 | 1.92 |
| Polyamide (2) | Example 2 | 9.8 ± 02.1 | 1.88 |
| Poly(1-vinylimidazole) | Example 3 | 12.4 ± 02.9 | 1.75 |
| Poly(4-vinylpyridine) | Example 4 | 9.4 ± 01.8 | 1.24 |
| Poly(2-vinylpyridine) | Example 5 | 10.9 ± 04.0 | 1.42 |
| Poly(9-vinylcarbazole) | Example 6 | 24.8 ± 03.6 | 4.00 |

Measurement of $Ce^{4+}/Ce^{3+}$ Ratio in Cerium Oxide Nanoparticle Whose Surface Is Covered with Polymer The ratio of $Ce^{4+}$ to $Ce^{3+}$ in the cerium oxide nanoparticle obtained in each of Examples 1 to 6 was measured by the X-ray photoelectron spectrometry (XPS) method. In the measurement, the excitation X-ray of the monocheomatic $AlK_{\alpha1,2}$ line (1,486.6 eV), the X-ray diameter of 200 μm, and the photoelectron escape angle of 45° were used. Before the measurement, the cerium oxide nanoparticles obtained in Examples 1 to 3 were freeze-dried in water after purification, and the cerium oxide nanoparticles obtained in Examples 4 to 6 were dried by a centrifugal evaporator after purification. The obtained values are listed in Table 1. Decomposition Test of Nucleic Acid Concentration of each solution of the nanoparticles prepared in Examples 1 to 6 and Comparative examples 1 was adjusted at 2 mg/mL. First, the concentration of our cerium oxide nanoparticle included in each solution of the nanoparticles prepared in Examples 1 to 6 was calculated as follows. Each solution of the nanoparticles prepared in Examples 1 to 6 was dropped onto a cover glass whose mass had been measured in advance, and then, this was heated on a hot plate. After this was cooled in an air, the mass of the cover glass was measured again. By obtaining the difference from the mass before heating, the mass of the cerium oxide nanoparticle was obtained. This mass was divided with the amount of the dropped solution to determine the concentration of the cerium oxide nanoparticle in the solution. On the basis of this concentration value, each of the concentrations of the cerium oxide nanoparticles was adjusted to be used in the experiments described below.

The aqueous solution (2 μL) of each of the cerium oxide nanoparticles prepared in Examples 1 to 3 and of the cerium oxide nanoparticle prepared in Comparative Example 1, 0.5 μL of the solution of 100 ng/μL pUC19 as the sample including the nucleic acid, and 2.5 μL of the 50 mM acetate buffer (pH 5) were added. Then, this mixture was allowed to statically leave at room temperature for 1 hour to carry out the decomposition reaction of the nucleic acid.

The 2 mg/mL dimethyl sulfoxide solution (2 μL) of each of the cerium oxide nanoparticles prepared in Examples 4 to 6, 0.5 μL of the solution of 100 ng/μL pUC19 as the sample including the nucleic acid, and 0.5 μL of the 150 mM acetate buffer (pH 5) were added, and then, this mixture was allowed to statically leave at room temperature for 1 hour to carry out the decomposition reaction of the nucleic acid.

As a control, 2 μL of water, 0.5 μL of 100 ng/μL pUC19, and 2.5 μL of the 50 mM acetate buffer (pH 5) were added. Then, this mixture was allowed to statically leave at room temperature for 1 hour.

To each of the solutions after the reaction were added 2 μL of 10% SDS (sodium dodecylsulfate polyacrylamide) and 3 μL of the 0.5 M phosphate buffer (pH 7) to carry out the electrophoresis with an agarose gel.

The agarose gel after the electrophoresis was dyed with ethidium bromide to detect the pUC19 bands. When the sample including the nucleic acid was contacted with the cerium oxide nanoparticle described in each of Examples 1 to 6 and Comparative Example 1, the pUC19 was cleaved, whereby the band of the closed circular structure of pUC19 and the new band of the open circular structure thereof were able to be recognized. On the other hand, in the control, the band of the open circular structure was not recognized, but only the band of the closed circular structure was recognized.

The band concentration (Y) of the closed circular structure in each solution was calculated, and the difference with the band concentration (X) of the closed circular structure in the control was calculated. Then, the ratio of this difference value to (X) was calculated as the decomposition rate. The results are listed in Table 2.

From these results, we confirmed that our cerium oxide nanoparticle can decompose the nucleic acid at a high decomposition rate.

On the other hand, cleavage of pUC19 were not able to be observed with the cerium oxide nanoparticle of Comparative Example 1.

TABLE 2

| Cerium oxide nanoparticle whose surface is covered with polymer | | Decomposition rate of nucleic acid [%] |
|---|---|---|
| Polyamide (1) | Example 1 | 78.3 |
| Polyamide (2) | Example 2 | 73.7 |
| Poly(1-vinylimidazole) | Example 3 | 82.2 |
| Poly(4-vinylpyridine) | Example 4 | 39.4 |
| Poly(2-vinylpyridine) | Example 5 | 58.1 |
| Poly(9-vinylcarbazole) | Example 6 | 51.6 |
| Polyacrylic acid | Comparative Example 1 | 7.4 |

Decomposition Test of Polypeptide

3 μL of the aqueous solution of our cerium oxide nanoparticle that had been prepared in Example 2 and the concentration of which had been adjusted to 0.2 mg/mL, 3 μL of 1 mg/mL ovalbumin (OVA) as the sample including the polypeptide, and 6 μL of the 50 mM acetate buffer (pH 5) were added. Then, this mixture was allowed to statically leave at 40° C. for 1 hour to carry out the decomposition reaction of the polypeptide.

As a control, 3 μL of sterilized distilled water, 3 μL of 1 mg/mL OVA, and 6 μL of the 50 mM acetate buffer (pH 5) were added. Then, this mixture was allowed to statically leave at 40° C. for 1 hour to carry out the decomposition reaction of the polypeptide.

To each of the solutions after the reaction was added 4 μL of NuPAGE LDS Sample Buffer (manufactured by Thermo Fisher Scientific Inc.). Then, this was heated at 95° C. for 10 minutes, and the electrophoresis with an acrylamide gel was carried out.

The acrylamide gel after the electrophoresis was dyed with Oriole (manufactured by Bio-Rad Laboratories, Inc.) to detect the OVA band. When the sample including the polypeptide was contacted with the cerium oxide nanoparticle described in Example 2, OVA was decomposed thereby resulting in decrease of the band concentration, and a smeared new band was recognized. On the other hand, in the control, the smeared band suggesting decomposition was not recognized.

The band concentration (X) of the control, and the band concentration (Y) of this Example at the same molecular weight position as the control were calculated, respectively. Then, the difference value between (X) and (Y) was calculated. The ratio of this difference value to (X) was calculated as the decomposition rate. The result thereof is listed in Table 3.

The decomposition reaction of the polypeptide by the cerium oxide nanoparticle prepared in Comparative Example 1 was also carried out with the same operation under the same condition as those described above to calculate the decomposition rate.

From this result, we confirmed that our cerium oxide nanoparticle can decompose the polypeptide at a high decomposition rate.

On the other hand, in the cerium oxide nanoparticle of Comparative Example 1, decomposition of the polypeptide was hardly recognized.

TABLE 3

| Cerium oxide nanoparticle whose surface is covered with polymer | | Decomposition rate of polypeptide [%] |
|---|---|---|
| Polyamide (2) | Example 2 | 82.7 |
| Polyacrylic acid | Comparative Example 1 | 17.2 |

Decomposition Test of Dye

30 μL of the aqueous solution of each of our cerium oxide nanoparticles that had been prepared in Examples 1 to 3 and the concentration of which had been adjusted to 2 mg/mL, 60 μL of 0.5 mg/mL Acid Orange 7 (AO7) as the sample including the organic dye, and 1.41 mL of distilled water were added. Then, this mixture was allowed to statically leave at 40° C. for 3 hours to carry out the decomposition reaction of the dye. As the control, the AO7 solution not including the cerium oxide nanoparticle was treated in the same way as above. After the reaction, 100 μL of the solution was taken and diluted with 1.9 mL of distilled water. Then, the absorption spectrum thereof was measured. With regard to the sample of the control, there was no change found in the absorption spectrum before and after the heating.

In the analysis, the absorbance at 485 nm, the wavelength at the maximum absorption of AO7, was used. The difference value in the absorbance between the control and this Example was calculated. Then, the ratio of this difference value to the absorbance at 485 nm of the control was calculated as the decomposition rate. The results are listed in Table 4.

The decomposition test of the dye by the cerium oxide nanoparticle prepared in Comparative Example 1 was also carried out with the same operation under the same condition as those described above to calculate the decomposition rate.

From this result, we confirmed that our cerium oxide nanoparticle can decompose the dye at a high decomposition rate. Because of such characteristics, our cerium oxide nanoparticle can be used as the oxidizing agent.

On the other hand, in the cerium oxide nanoparticle of Comparative Example 1, decomposition of the dye was hardly recognized.

TABLE 4

| Cerium oxide nanoparticle whose surface is covered with polymer | | Decomposition rate of coloring matter [%] |
|---|---|---|
| Polyamide (1) | Example 1 | 60 |
| Polyamide (2) | Example 2 | 62 |
| Poly(1-vinylimidazole) | Example 3 | 54 |
| Polyacrylic acid | Comparative Example 1 | 6 |

Measurement of Oxidase Activity

TMBZ was dissolved into an aqueous 90% DMSO solution; then. Then, the dilution series of 10, 5, 2.5, 1.25, and 0.625 mM were prepared. One hundred and 60 μL of the 50 mM citrate buffer (pH 4) and 20 μL of the TMBZ solution with each concentration were mixed. Then, the resulting mixture was added to the 96-wells plate. To this was added 20 μL of each of the aqueous solutions of the cerium oxide nanoparticles that had been prepared in Examples 1 to 3 and the concentration of which had been adjusted to 2 mg/mL. Then, immediately thereafter, this was set to the plate reader to measure the temporal change of the absorbance at 652 nm due to coloring of TMBZ to a blue color with the measurement interval of 30 seconds and the measurement period of 10 minutes.

For calculation of the oxidase activity, the Michaelis Menten equation was used. Because there was no change in the nanoceria concentration, the steady state approximation was performed in this oxidase activity measurement to obtain the Michaelis Menten constant Km and the maximum reaction rate Vmax. In analysis of the Michaelis Menten equation, the Lineweaver plot (double reciprocal plot) was used. Among the results obtained, the maximum reaction rate Vmax, the value indicating the oxidase activity, is listed in Table 5.

The oxidase activity measurement of the cerium oxide nanoparticle prepared in Comparative Example 1 was also carried out with the same operation under the same condition as those described above to calculate the maximum reaction rate Vmax.

From this result, we confirmed that our cerium oxide nanoparticle has a high oxidase activity. Because of such characteristics, our cerium oxide nanoparticle can be used as the oxidizing agent.

On the other hand, in the cerium oxide nanoparticle of Comparative Example 1, the oxidase activity was lower than the values of the cerium oxide nanoparticles of Examples 1 to 3.

TABLE 5

| Cerium oxide nanoparticle whose surface is covered with polymer | | Oxidase activity Vmax [μM/sec] |
|---|---|---|
| Polyamide (1) | Example 1 | 5.4 |
| Polyamide (2) | Example 2 | 1.3 |
| Poly(1-vinylimidazole) | Example 3 | 1.2 |
| Polyacrylic acid | Comparative Example 1 | 0.7 |

Measurement of Catalase Activity

The catalase activity was measured by using Amplex Red Catalase Assay Kit (A22180) manufactured by Thermo Fisher Scientific Inc. in accordance with the protocol. To describe simply, 50 μL of Reaction Buffer, 25 μL each of our cerium oxide nanoparticles that had been prepared in Examples 1 to 3 and the concentration of which had been adjusted to 16 μg/mL, and 25 μL of the aqueous 40 μM hydrogen peroxide solution were mixed. Then, the resulting mixture was allowed to statically leave for 30 minutes to carry out the decomposition reaction of hydrogen peroxide. The reaction solution was passed through the 30 kD ultrafiltration membrane. Then, 100 μL of the flow-through solution was mixed with 50 μL of Working Solution to carry out the reaction at 37° C. for 30 minutes. The resorufin generated by the reaction was excited at 544 nm, and the fluorescence intensity at 590 nm was measured. By comparing with the calibration curve prepared by the catalase standard whose active value had already been known, the catalase activity of the cerium oxide nanoparticle was calculated. The results thereof are listed in Table 6.

The catalase activity measurement of the cerium oxide nanoparticle prepared in Comparative Example 2 was also carried out with the same operation under the same condition as those described above to calculate the catalase activity.

From this result, we confirmed that our cerium oxide nanoparticle has a high catalase activity. Because of such characteristics, our cerium oxide nanoparticle can be used as the antioxidant.

On the other hand, in the cerium oxide nanoparticle of Comparative Example 2, the catalase activity was lower than the values of the cerium oxide nanoparticles of Examples 1 to 3.

TABLE 6

| Cerium oxide nanoparticle whose surface is covered with polymer | | Catalase activity [U/mL] |
|---|---|---|
| Polyamide (1) | Example 1 | 0.7 |
| Polyamide (2) | Example 2 | 1.0 |
| Poly(1-vinylimidazole) | Example 3 | 0.6 |
| CA/EDDS | Comparative Example 2 | 0.3 |

Retention Test of Dye by Radical Scavenging

100 µL of the aqueous 1 mM iron (II) chloride solution and 100 µL of the aqueous 1 mM hydrogen peroxide solution were mixed, and then, to this mixed solution was added 10 µL of the solution of our cerium oxide nanoparticle that had been prepared in each of Examples 1 to 3 and the concentration of which had been adjusted to 0.4 mg/mL. Then, the resulting mixture was allowed to be statically leave at room temperature for 5 minutes. To this mixed solution was added 90 µL of the aqueous 100 µM methylene blue solution. Then, this was allowed to be statically leave at room temperature for 25 minutes. As a control, the same treatment was carried out to the solution not including the cerium oxide nanoparticle. The standard solution was prepared by mixing 90 µL of the aqueous 100 µM methylene blue solution with 210 µL of distilled water. Then, the absorption spectra of these solutions were measured.

For the analysis, the absorbance at 664 nm, the wavelength of the maximum absorption of the methylene blue, was used. The difference ($\Delta I_0$) between the absorbance ($I_0$) of the standard solution and the absorbance ($I_c$) of the control, and the difference ($\Delta I$) between the absorbance (I) of each of Examples 1 to 3 and the absorbance ($I_c$) of the control were calculated. The ratio of the latter ($\Delta I$) to the former ($\Delta I_0$) was calculated as the decomposition rate; and this was taken as the dye retention rate. The results are listed in Table 7.

With regard to the 0.4 mg/mL cerium oxide nanoparticle prepared in Comparative Example 1, the retention test of the dye was also carried out with the same operation under the same condition as those described above to calculate the dye retention rate.

From this result, we confirmed that our cerium oxide nanoparticle can scavenge the radical. Because of such characteristics, our cerium oxide nanoparticle can be used as the antioxidant.

On the other hand, in the cerium oxide nanoparticle of Comparative Example 1, the dye retention rate was lower than the cerium oxide nanoparticles of Examples 1 to 3.

TABLE 7

| Cerium oxide nanoparticle whose surface is covered with polymer | | Coloring matter retention rate [%] |
|---|---|---|
| Polyamide (1) | Example 1 | 62 |
| Polyamide (2) | Example 2 | 90 |
| Poly(1-vinylimidazole) | Example 3 | 63 |
| Polyacrylic acid | Comparative Example 1 | 23 |

Antifungal Test

Figure 3:
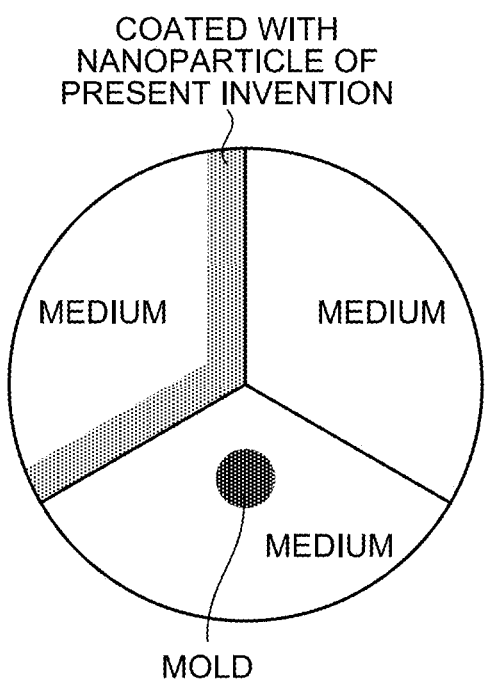
FIG. 3 is the drawing to explain the antifungal test in Example 2.

The solution of our cerium oxide nanoparticle that had been prepared in Example 2 and the concentration of which had been adjusted to 2 mg/mL was passed through the 0.45 µm sterilizing filter. As illustrated in FIG. 3, the potato dextrose agar medium (PDA medium) was divided into 3 compartments. Then, after the cerium oxide nanoparticle solution was applied in the boundary area of one compartment to other compartments, this was dried with an air in a clean bench for 30 minutes. *Trichoderma* (QM9414 strain (NBRC 31329); heretofore known mutant belonging to *Trichoderma*) was inoculated to the medium on one compartment other than the coated compartment, which was then followed by culturing at 28° C. to evaluate whether the growth of the mold was able to be suppressed due to the coated surface of our nanoparticle.

Figure 4:
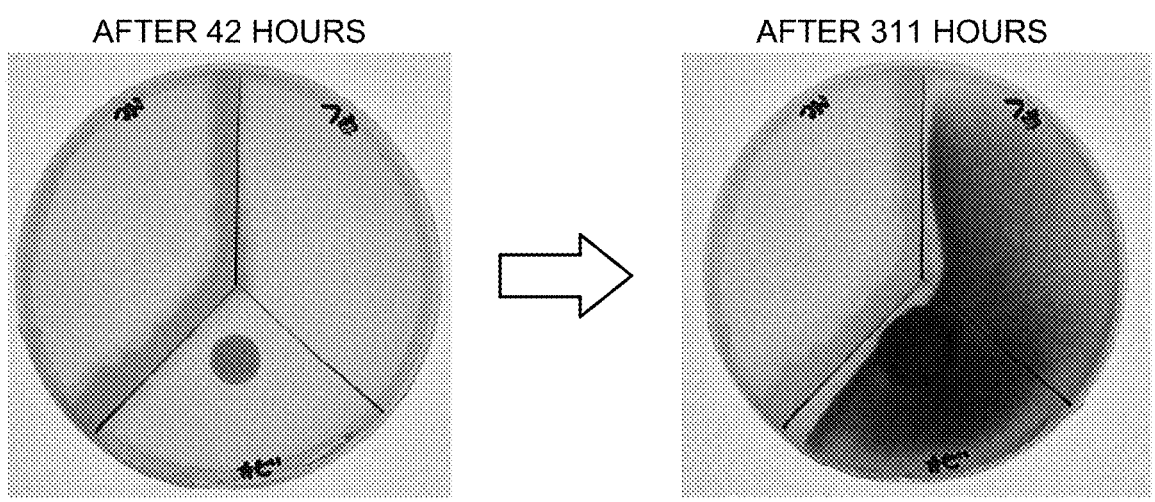
FIG. 4 is the drawing to explain the result of the antifungal test in Example 2.
Figure 5:
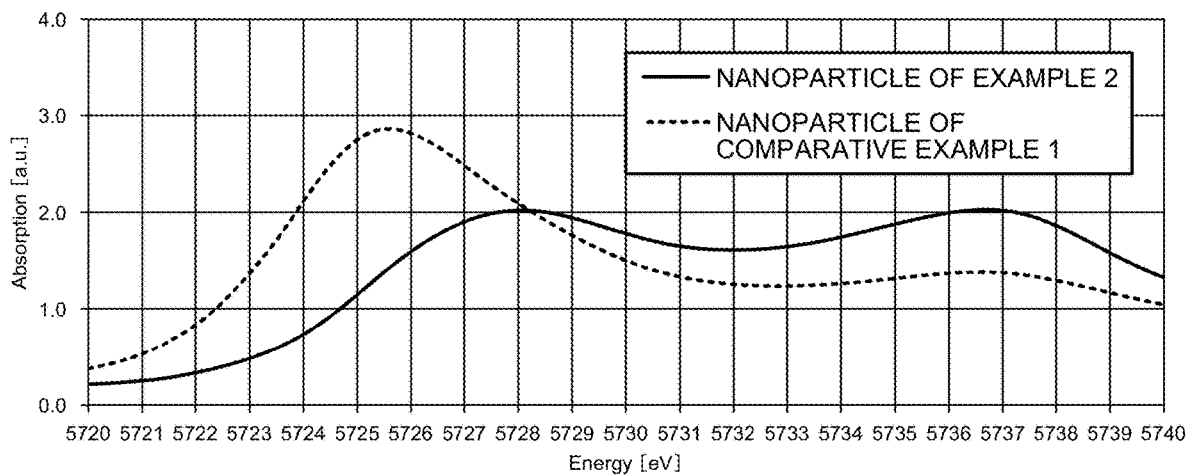
FIG. 5 is the Ce L3 edge XANES spectra of the cerium oxide nanoparticle prepared in Example 2 and the cerium oxide nanoparticle prepared in Comparative Example 1.
Figure 6:
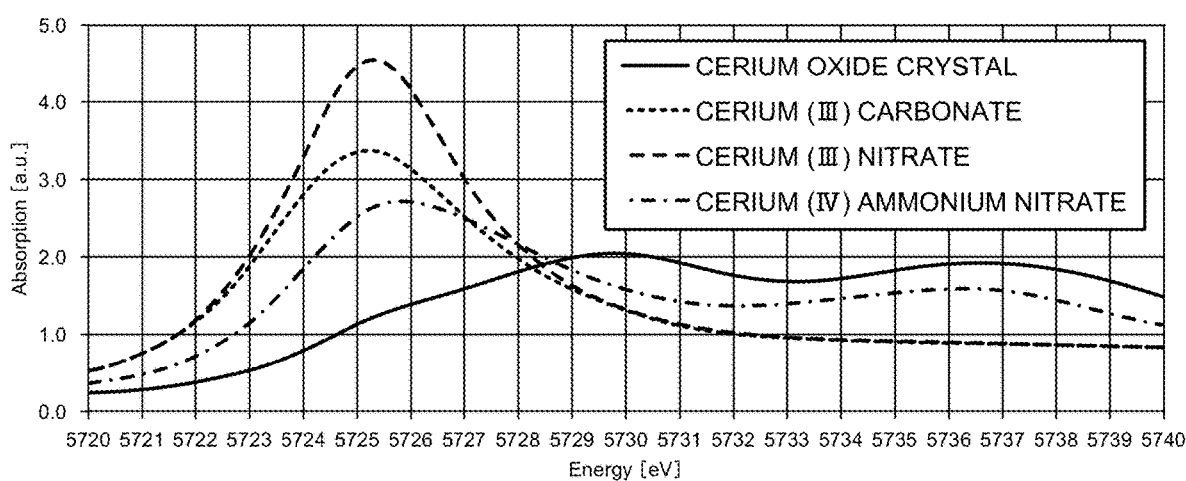
FIG. 6 is the Ce L3 edge XANES spectra of the cerium oxide crystal, cerium (III) carbonate, cerium (III) nitrate, and cerium (IV) ammonium nitrate prepared in Reference Example 1.

The result is illustrated in FIG. 4. Growth of the mold was recognized after 42 hours from the start of culturing. After 311 hours, growth of the mold was observed to be stopped on the surface that had been coated with our nanoparticle From this result, we confirmed that our cerium oxide nanoparticle can exhibit the antifungal performance.

Inactivation Test of Virus

This test was carried out in Kitasato Research Center for Environmental Science. With 0.1 mL of the virus solution (feline calicivirus F-9, ATCC, VR-782, substitute of norovirus), 0.9 mL of the solution of our cerium oxide nanoparticle that had been prepared in Example 2 and the concentration of which had been adjusted to 10 mg/mL was mixed and the virus acted for 1 hour. Then, PBS was added as the action-stopping solution so that the action to the virus was stopped. The infectivity titer was measured with the TCID50 method by using this solution as the original solution of the sample to measure the virus value.

The logarithmic reduction value of the infectivity titer to the infectivity titer before applying our cerium oxide nanoparticle is listed in Table 8.

With regard to the solution of the cerium oxide nanoparticle prepared in Comparative Example 1, the inactivation test of the virus was also carried out with the same operation under the same condition as those described above to calculate the logarithmic reduction value of the infectivity titer. This result is listed in Table 8.

Because the logarithmic reduction value was 4.0 in this result, we confirmed that our cerium oxide nanoparticle has 99.99% of the anti-virus activity.

On the other hand, in the cerium oxide nanoparticle of Comparative Example 1, the logarithmic reduction value was −0.4, indicating that this has a low virus inactivation performance.

TABLE 8

| Cerium oxide nanoparticle whose surface is covered with polymer | | Infectivity titer logarithmic reduction value [%] |
|---|---|---|
| Polyamide (2) | Example 2 | 4.0 |
| Polyacrylic acid | Comparative Example 1 | −0.5 |

XAFS Observation)

An X-ray was irradiated to the solution of our cerium oxide nanoparticle that had been prepared in Example 2 and the concentration of which had been adjusted to 10 mg/mL to measure the absorption amount thereof, thereby measuring the X-ray absorption fine structure (XAFS) spectrum. The measurement was carried out at High Energy Accelerator Research Organization Synchrotron Radiation Research Center (Photon Factory) BL12C using the Si(111) double crystal spectrometer with the Ce L3 absorption edge, by the transmission detection method, and with the ion chamber detector.

The Ce L3 edge XANES spectrum is illustrated in FIG. 5. In the spectrum, the absorption edge (EO) was set at 5,724.4 eV, in which the vertical axis was the ratio based on 0 as the average absorption in the range of −150 eV to −30 eV from EO, and 1 as the average absorption in the range of +150 eV to +400 eV from EO.

With regard to the solution of the cerium oxide nanoparticle prepared in Comparative Example 1, the XAFS observation was also carried out with the same operation under the same condition as those described above. The Ce L3 edge XANES spectrum thus obtained is exhibited in FIG. 5.

From this result, it can be seen that our cerium oxide nanoparticle has the maximum absorptions at 5,728.003 eV from 5,726.0 eV to 5,729.0 eV, and at 5,736.582 eV from 5,735.0 eV to 5,739.0 eV.

On the other hand, it can be seen that the cerium oxide nanoparticle of Comparative Example 1 has the maximum absorptions at 5,725.631 eV and 5,736.582 eV. So, this has the maximum absorption from 5,735.0 eV to 5,739.0 eV, but does not have the maximum absorption from 5,726.0 eV to 5,729.0 eV.

Reference Example 1: XAFS Observation

The XAFS observation was carried out with the same operation under the same condition as those of XAFS observations in Examples 1 to 3 as described above, except that the cerium oxide crystal, which is not the nanoparticle, cerium (III) carbonate, cerium (III) nitrate, or cerium (IV) ammonium nitrate, which are cerium salts, were used. The Ce L3 edge XANES spectra of them are exhibited in FIG. 6. We found that the cerium oxide crystal had the maximum absorptions at 5,729.751 eV and 5,736.582 eV, cerium (III) carbonate had the maximum absorption at 5,725.161 eV, cerium (III) nitrate had the maximum absorption at 5,725.316 eV, and cerium (IV) ammonium nitrate had the maximum absorptions at 5,725.796 eV and 5,736.105 eV; but that none of the heretofore known cerium salts and the cerium compounds had the maximum absorptions from 5,726.0 eV to 5,729.0 eV and from 5,735.0 eV to 5,739.0 eV.

The invention claimed is:

1. A cerium oxide nanoparticle comprising:

a center nucleus formed of a mixture of $Ce_2O_3$ and $CeO_2$; and a polymer layer covering the center nucleus, the polymer layer being formed of a vinyl polymer having a heterocyclic amine skeleton or of a polyamide having a heterocyclic amine skeleton, wherein a ratio of $Ce^{4+}$to $Ce^{3+}$is 1.24 to 4.00.

2. The cerium oxide nanoparticle according to claim 1, wherein the heterocyclic amine skeleton is formed of any of piperazine, pyridine, imidazole, or carbazole.

3. The cerium oxide nanoparticle according to claim 1, wherein the vinyl polymer is a polymer having the heterocyclic amine skeleton in a side chain of the vinyl polymer.

4. The cerium oxide nanoparticle according to claim 1, wherein the polyamide is a polymer having the heterocyclic amine skeleton in a main chain of the polyamide.

5. A decomposition method of a nucleic acid, comprising causing a sample including the nucleic acid to contact with the cerium oxide nanoparticle according to claim 1.

6. A decomposition method of a polypeptide, comprising causing a sample including the polypeptide to contact with the cerium oxide nanoparticle according to claim 1.

7. An oxidizing agent comprising the cerium oxide nanoparticle according to claim 1.

8. An antioxidant comprising the cerium oxide nanoparticle according to claim 1.

9. An antifungal agent comprising the cerium oxide nanoparticle according to claim 1.

10. An anti-virus agent comprising the cerium oxide nanoparticle according to claim 1.

11. The cerium oxide nanoparticle according to claim 1, wherein a Ce L3 edge XANES spectrum obtained by an X-ray absorption fine structure spectrometry measurement has a maximum absorption of 5726.0 eV to 5729.0 eV and 5735.0 eV to 5739.0 eV.

12. A method of producing the cerium oxide nanoparticle according to claim 1, the method comprising:

a) mixing a solution of a polymer having a heterocyclic amine skeleton with a solution including a cerium (III) ion or with a cerium (III) salt to obtain a mixed solution; and b) adding an oxidizing agent to the mixed solution obtained at the process a).

* * * * *